United States Patent [19]

Gianpaolo

[11] Patent Number: 5,678,732
[45] Date of Patent: Oct. 21, 1997

[54] PROCESS FOR MAKING CONTAINER OF PLASTICIZED SHEET MATERIAL AND CONTAINER OBTAINED WITH THIS PROCESS

[76] Inventor: Belloli Gianpaolo, Via del Falco 3, Rastignano (Bologna), Italy

[21] Appl. No.: 536,374

[22] Filed: Sep. 29, 1995

[51] Int. Cl.⁶ ............................................. B65D 35/08
[52] U.S. Cl. ........................ 222/107; 493/87; 493/102; 493/212; 53/133.2
[58] Field of Search ......................... 222/107, 211, 222/215, 464.1, 527, 529, 573, 574, 566, 83; 493/87, 102, 212, 927; 53/133.2, 374.9, 375.2

[56] References Cited

U.S. PATENT DOCUMENTS

| | | | |
|---|---|---|---|
| 3,105,613 | 10/1963 | Barton et al. | 222/107 |
| 3,263,848 | 8/1966 | Zackheim | 222/107 |
| 4,718,778 | 1/1988 | Ichikawa . | |
| 4,876,788 | 10/1989 | Steer . | |
| 5,226,564 | 7/1993 | Steer et al. | 222/107 |

FOREIGN PATENT DOCUMENTS

| | | |
|---|---|---|
| 451 380 | 7/1943 | Belgium . |
| 2 659 600 | 3/1990 | France . |
| 2 241 487 | 4/1991 | United Kingdom . |
| WO 82/01682 | 5/1982 | WIPO . |

*Primary Examiner*—Philippe Derakshani
*Attorney, Agent, or Firm*—McAulay Fisher Nissen Goldberg & Kiel, LLP

[57] ABSTRACT

A process for making a container of heat-sealable plasticized sheet material, provided with a pouring spout and formed of a pair of facing walls having two side edges connected to each other by side walls folded to create side bellows. The process comprises the steps of sealing the upper edges of the facing walls so as to define an opening, of providing a small tube of a rigid material fitted with a flange that extend wider than the opening and that defines the spout and a thin cane, of inserting the thin cane into the container through the opening till the flange meets the border of the upper sealed edges, of folding said flange on the outer faces of the facing walls to cover the edges, and of tight sealing the flange to the edges.

7 Claims, 2 Drawing Sheets

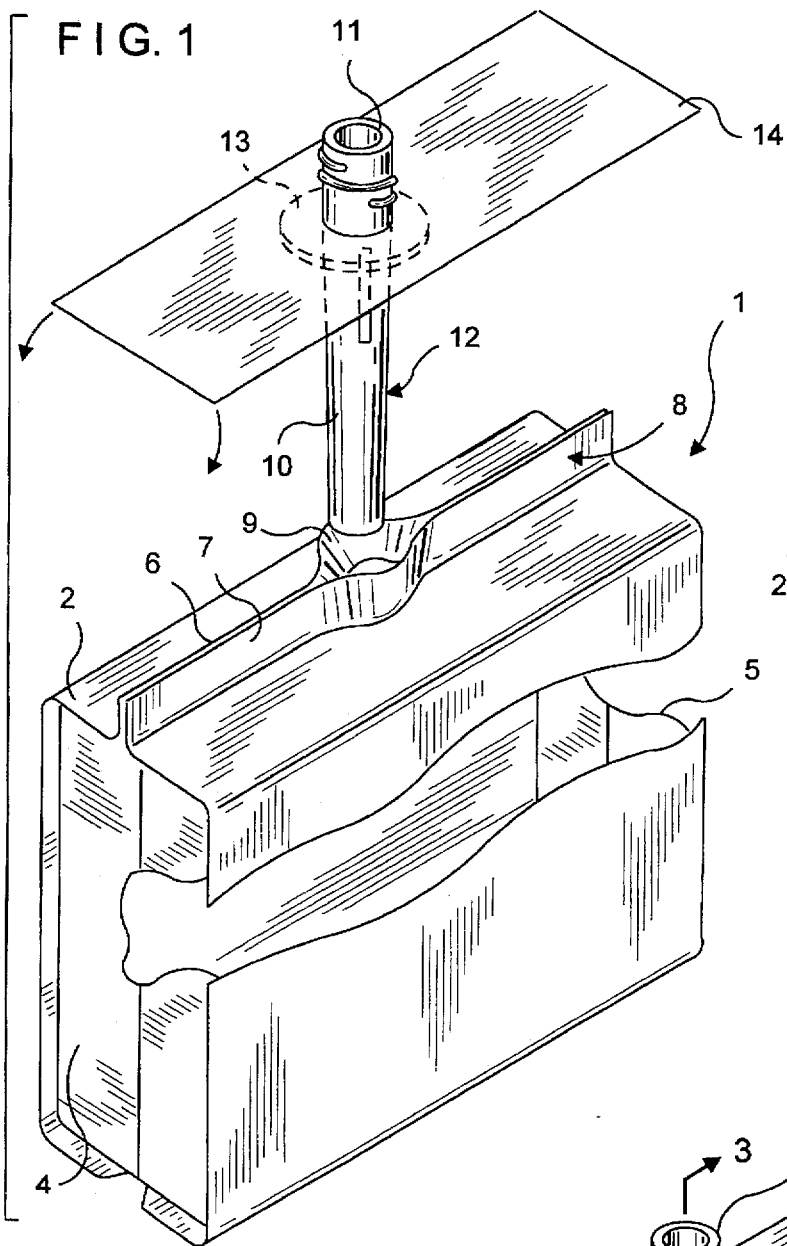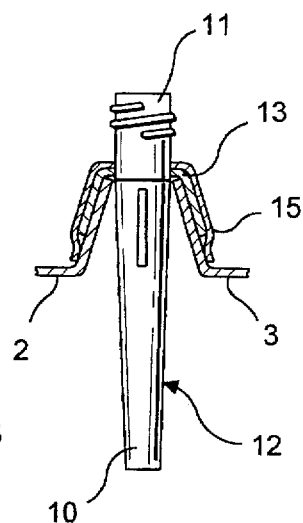

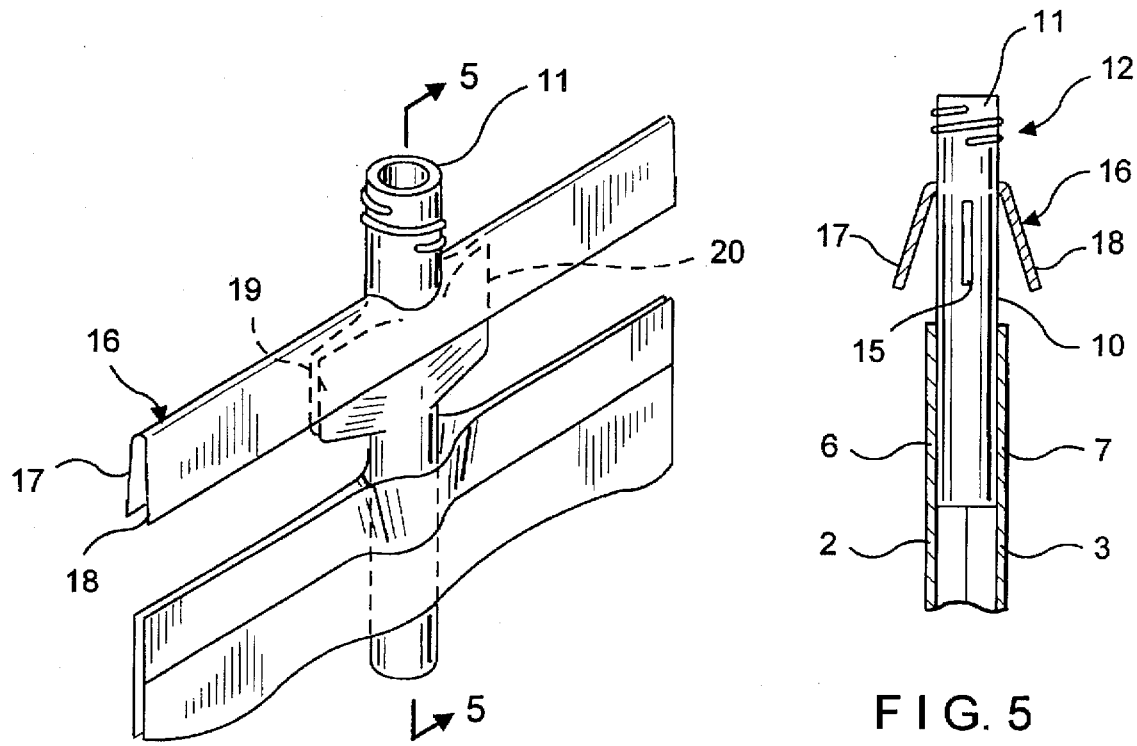
FIG. 4
FIG. 5
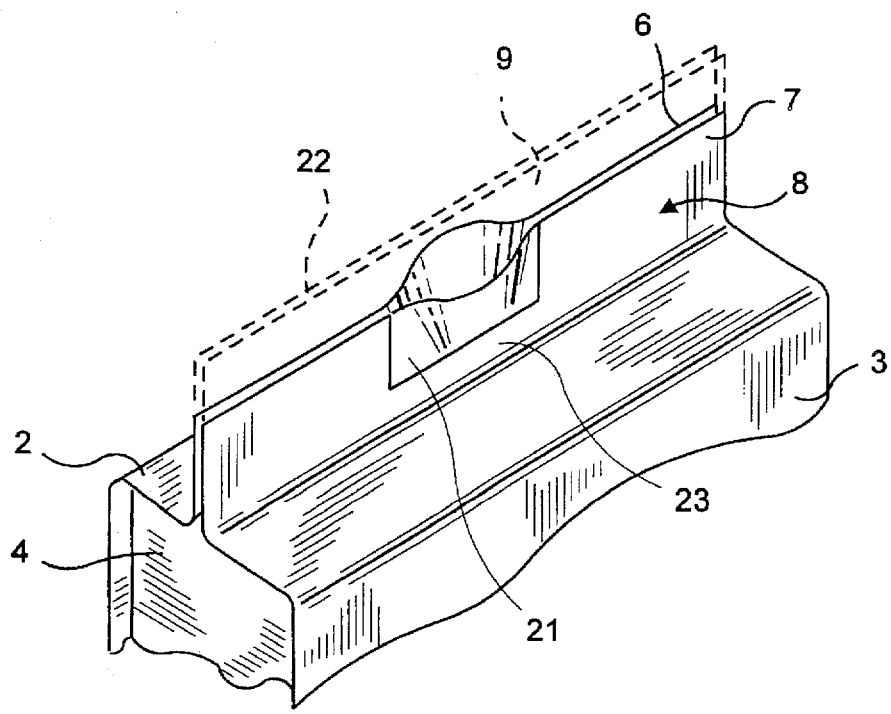
FIG. 6

PROCESS FOR MAKING CONTAINER OF PLASTICIZED SHEET MATERIAL AND CONTAINER OBTAINED WITH THIS PROCESS

FIELD OF THE INVENTION

The present invention concerns a process for making containers in plasticized sheet material provided with pouring spout, as well as the container obtained with this process.

BACKGROUND OF THE INVENTION

On the market, containers exist made of plasticized sheet material comprising two facing walls whose side edges are connected by side walls. The side walls are folded down middle between the facing walls so as to make two side bellows which, during the filling operation, allow the container to expand to assume a pseudo-prismatic shape suitable to allow the container to stand up when it is placed on a flat surface.

The container is provided with a spout which allows the liquid inside the container to be poured and sipped; this spout is made up of a thin cane of a rigid plastic material which is inserted between the two edges where the two facing walls of the container join at the top. The closure of the container is made by sealing the two edges to each other and around the thin cane.

It has been observed that this closure causes a notable percentage of waste which makes the container economically disadvantageous. In fact retaining deficiencies have frequently been found, in the sealing area next to the spout, which often remain invisible while the container is manufactured but are noted during the subsequent filling phase.

OBJECT OF THE INVENTION

It is therefore the object of the present invention is to propose a new process to avoid the above-mentioned drawbacks characteristic of the current manufacturing techniques.

SUMMARY OF THE INVENTION

This task is achieved with a process for making a container of heat-sealable plasticized sheet material, provided with a pouring spout, said container being formed of a pair of facing walls having two side edges connected to each other by means of side walls folded to create side bellows and said process is characterized by the fact that it comprises the steps of: sealing the upper edges of said facing walls so as to define an opening; providing a small tube of a rigid material fitted with a flange that extends wider than said opening and that defines said spout and a thin cane; inserting said thin cane into said container through said opening till said flange meets the border of said upper sealed edges; folding said flange on the outer faces of said facing walls to cover said edges; and tight sealing said flange to said edges.

The purpose of the present invention is to devise a container which can be made with said new process.

This purpose is achieved with a container of heat-sealable plasticized sheet material fitted with a pouring spout and formed of a pair of facing walls having two side edges sealed to side walls folded to create side bellows and two upper edges sealed to each other, said spout being fitted with a thin cane which extends inside said container through said sealed edges and being characterized by the fact that a folded and liquid-tight flange covering said upper edges is an integral part of said spout.

BRIEF DESCRIPTION OF THE DRAWINGS

The invention will be described and explained in detail in the following description, in which further particularities will result, with reference to the enclosed drawings, in which:

FIG. 1 shows a perspective view of a container during a manufacturing step;

FIG. 2 shows the container;

FIG. 3 shows a sectional view along the line III—III of FIG. 2;

FIG. 4 shows a view of a further container during a manufacturing step;

FIG. 5 shows a sectional view along the line V—V of FIG. 4;

FIG. 6 shows a perspective view of another embodiment of the container.

SPECIFIC DESCRIPTION

With reference to the FIGS. 1 to 3, reference numeral 1 indicates a container which includes two facing walls 2,3 between the edges of which two side walls 4,5 are placed.

Both facing walls 2,3 and side walls 4,5 are made of flexible sheet material. In particular said sheet material may be formed of one or more layers of which the one that remains inside the container is heat-sealable.

The said walls 4,5 are folded down the middle so as to create a kind of bellows which allow the container to expand as it is being filled with the beverage and to assume a parallelepipedal shape. The manufacturing technique of said containers is already known so it will not be described further in detail since it does not constitute the object of the present invention.

An important element of the present invention is the previous joining of the upper edges 6, 7 of the walls 2, 3 by making a seal 8 to close the container except for a central area in which is defined an opening 9.

The thin cane 10 of a small tube 12 made of plastic material sufficiently stiff for the purpose of the present invention is inserted through said opening.

The thin cane 10 is separated from a spout 11 by means of a collar 13 forming a single block with the same thin cane.

The spout 11 is provided with an outer thread for the screwing of a closing cap. On the collar 13 a rectangular piece of sheet material is applied so as to obtain a flange 14. The flange material is suitable to be sealed onto the outer surfaces of the walls 2, 3. In this way, after having inserted the thin cane 10 through the opening 9 till the borders of the edges 6, 7 meet under the collar 13 and after having folded the side flaps of the flange 14 onto the outer faces of the walls of the edges 6, 7, it is possible to seal said flaps to the upper edges 6, 7 so obtaining a perfectly hermetically-sealed container.

In this way the described invention perfectly fulfils the established purposes. In particular the flange 14 allows a sealing line to be made which is able to guarantee a perfect seal by joining two sheet materials that have a thermal compatibility.

One advantage is that the collar 13 allows the edges 6, 7 of the walls 2, 3 to be kept away from the thin cane 10, in such a way to make the complete emptying of the container easier through pouring slots 15 which are made in the thin cane, immediately under the collar 13.

Many modifications and changes are possible in the actual embodiment of the invention, while the same inventive concept comprises all of them.

FIGS. 4, 5 show a solution where there is a flange 16 which is made as an integral part of the small tube 12. The flange 16 is pre-formed in such a way as to have two flaps 17, 18 positioned like an inverted V, to be placed upon the edges 6,7.

Another advantage is that, from the thin cane 10, in the area which is comprised between the flaps 17, 18 two tabs 19, 20 are extending diametrically. When the small tube 12 is inserted in the opening 9, the two tabs are simultaneously inserted between the edges 6,7 to contrast the sealing pressure. Preferably the two tabs 19, 20 are connected to the thin cane to avoid the creation of corners which could cause problems to the seal.

An advantage of this invention must be seen in the fact that the opening 9, which is very small in size, prevents the liquid from escaping when the containers are filled before joining the small tube 12.

Moreover, according to an embodiment of the present invention shown in FIG. 6, it is possible to integrally seal the upper edges of the walls to each other except for an intermediate area 21.

Taking away the upper marginal part 22 of the seal 8, an opening 9 is defined between the two flaps of the area 21, said opening is closed along its bottom by a thin sealing strip 23. This determines the formation of a completely-sealed and liquid-tight container, but the application of the small tube is still possible by making one end of the thin cane in a point-shape and punching the sealing strip 23.

What is claimed is:

1. A process for making a container of heat-sealable plasticized sheet material, provided with a pouring spout, said container being formed of a pair of facing walls having two side edges connected to each other by means of side walls folded to create side bellows, the process comprising the steps of:

sealing the upper edges of said facing walls so as to define an opening;

providing a small tube of a rigid material fitted with a flange that extends wider than said opening and that defines said spout and a thin cane;

inserting said thin cane into said container through said opening till said flange meets the border of said upper sealed edges;

folding said flange on the outer faces of said facing walls to cover said edges;

tight sealing said flange to said edges.

2. A process according to claim 1 wherein said flange is formed of a collar integral with said small tube and by a portion of sheet material sealed to said collar and heat sealable upon said edges.

3. A process according to claim 1 wherein said flange is formed in a single block with the small tube, and said flange is pre-shaped in an inverted V to be placed upon said upper edges.

4. A process according to claim 2 wherein two diametrical tabs are integral with said small tube for placement between said upper edges.

5. A process according to claim 3 wherein two diametrical tabs are integral with said small tube for placement between said upper edges.

6. A process according to claim 1 wherein said upper edges are sealed together except for a central area, and that a marginal part of the seal is taken away so that the flaps of said area define an opening, closed by a thin sealing strip and wherein the thin cane of said small tube is inserted in said sealing strip, the sealing strip perforated by the thin cane.

7. A container of formed heat sealable plasticized sheet material having a pouring spout, the container comprising a pair of facing walls having two side edges, connected to each other by means of sidewalls, the sidewalls folded to create side bellows, two upper edges of the facing walls being sealed to each other, a thin cane extending through the sealed edges into the container to define the spout, a folded flanged being integral with the spout and located over outer faces of the facing walls to cover the upper sealed edges, the folded flange tight sealing the upper sealed edges together.

* * * * *